US007897604B2

(12) United States Patent
Lamango

(10) Patent No.: US 7,897,604 B2
(45) Date of Patent: Mar. 1, 2011

(54) INHIBITORS OF POLYISOPRENYLATED METHYLATED PROTEIN METHYL ESTERASE

(75) Inventor: Nazarius Saah Lamango, Tallahassee, FL (US)

(73) Assignee: Florida Agricultural and Mechanical University, Tallahassee, FL (US)

( * ) Notice: Subject to any disclaimer, the term of this patent is extended or adjusted under 35 U.S.C. 154(b) by 199 days.

(21) Appl. No.: 12/098,712

(22) Filed: Apr. 7, 2008

(65) Prior Publication Data
US 2009/0253640 A1    Oct. 8, 2009

(51) Int. Cl.
  *A61K 31/497*    (2006.01)
  *C07F 9/02*    (2006.01)
(52) U.S. Cl. .................................. 514/252.13; 544/243
(58) Field of Classification Search ............. 514/252.13; 544/243
  See application file for complete search history.

(56) References Cited

U.S. PATENT DOCUMENTS

| 5,202,456 | A | * | 4/1993 | Rando | 558/438 |
| 5,574,025 | A | | 11/1996 | Anthony et al. | |
| 5,705,528 | A | | 1/1998 | Kloog | |
| 6,372,793 | B1 | * | 4/2002 | Lamango et al. | 514/562 |

OTHER PUBLICATIONS

Anderegg, et al, "Structure of Saccaromyces Cerevusuae Mating Hormone A-Factor, Identification of S-Farnesyl Cysteine as a Structural Component," J Biology Chemistry, 263:18236-18240 (1988).
Anderson, et al, "Purification, Functional Reconstitution and Characterization of the Saccharomyces Cerevisiae Isoprenylcysteine Carboxylmethyltransferase" Ste 14p. J Biology Chemistry 280: 7336-7345 (2005).
Ascherio, et al, "Pesticide Exposure and Risk for Parkinson's Disease." Ann Neurol 60: 197-203 (2006).
Becker, et al, "Synthesis and Structure-Activity Relationships of Beta-and Alpha-Piperidine Sulfone Hydroxamic Acid Matrix Metalloproteinase Inhibitors with Oral Antitumor Efficacy." J Med Chem 48: 6713-6730 (2005).
Bergo, et al, "Isoprenylcysteine Carboxyl Methyltransferase Deficiency in Mice." J Biol Chem 276: 5841-5845 (2001).
Bifulco, "Role of the Isoprenoid Pathway in *ras* Transforming Activity, Cytoskeleton Organization, Cell Prolkiferation and Apoptosis," Life Sciences, 77 1740-1749 (2005).
Brown et al., "Prenylated Proteins. A Convenient Synthesis of Farnesyl Cysteinyl Thioesters," J. Am. Chem. Soc., 113, 3176-3177 (1991).
Calero, et al, "Saccharomyces Cerevisiae Pra1p/Yip3p Interacts with Yip1p and Rab Proteins." Biochem Biophys Res Commun, 290: 676-681 (2002).
Capdevila, et al, "Pancreatic Exocrine Secretion is Blocked by Inhibitors of Methylation." Arch Biochem Biophys 345: 47-55 (1997).

Chen, et al., "G Protein β2 Subunit Interacts Directly with Neuropathy Target Esterase and Regulates its Activity," Intl. J. Biochem. & Cell Biology 39, 124-132 (2007).
Cohen, et al, "Inhibitors of Prenylation of Ras and Other G-Proteins and Their Application as Therapeutics." Biochem Pharmacol 60: 1061-1068 (2000).
Costa, "Current Issues in Organophosphate Toxicology." Clin Chem Acta 366: 1-13 (2006).
Dietrich, et al, "Isoprenylation of the G Protein Gamma Subunit is Both Necessary and Sufficient for Beta Gamma Dimmer-Mediated Stimulation of Phospholipase." C. Biochemistry 35:15174-15182 (1996).
Ding, et af, "Farnesyl-L-Cysteine Analogs Can Inhibit or Initiate Superoxide Release by Human Neutrophils." J Biol Chem 269:16837-16844 (1994).
Dolence, et al, "A Mechanism for Posttranslational Modifications of Proteins By Yeast Protein Farnesyltransferase." Proc National Acad Sci U S A 92: 5008-5011 (1995).
Ehrhardt, et al, "Ras and Relatives—Job Sharing and Networking Keep An Old Family Together." Exp Hematol 30:1089-1106 (2002).
Glynn, "Neuropathy Target Esterase and Phospholipids Deacylation." Biochim Biophys Acta 1736: 87-93 (2005).
Gosser, et al, "C-Terminal Binding Domain of Rho GDP-Dissociation Inhibitor Directs N-Terminal Inhibitory Peptide to GTPases." Nature 387: 814-819 (1997).
Khosravi-Far, et al, "Ras (CXXX) and Rab (CC/CXC) Prenylation Signal Sequences are Unique and Functionally Distinct." J Biol Chem 267: 24363-24368 (1992).
Kloog et al., "Prenyl-Binding Domains: Potential Targets for Ras Inhibitors and Anti-Cancer Drugs," Seminars in Cancer Biology 14, 253-261 (2004).
Lamango, et. al, "Quantification of S-Adenosylemethionine-Induced Tremors: A Possible Tremor Model for Parkinson's Disease," Pharmacology Biochemistry and Behavior, 65:3, 523-529 (2000).
Lamango, "Liver Prenylated Methylated Protein Methyl Esterase Is an Organophosphate-Sensitive Enzyme," J. Biochem. Molecular Toxicology, 19:5 347-357 (2005).
Lebowitz, et al, "Farnesyltransferase Inhibitors Alter the Prenylation and Growth-Stimulating Function of RhoB." J Biol Chem 272: 15591-15594 (1997).
Lutz, et al, "Feedback Inhibition of Polyisoprenyl Pyrophosphate Synthesis From Mevalonate In Vitro. Implication for protein prenylation." J Biol Chem 267: 7983-7986 (1992).
Ma, et al, "Mechanistic Studies on Human Platelet Isoprenylated Protein Methyltransferase: Farnesylcysteine Analogs Block Platelet Aggregation Without inhibiting the Methyltransferase." Biochemistry 33: 5414-5420 (1994). Marom, et al, "Selective Inhibition of Ras-Dependent Cell Growth by Farnesylthiosalisylic Acid." J Biol Chem 270: 22263-22270 (1995).
Martincic, et al, "Isolation and Characterization of a Dual Prenylated Rab and VAMP2 Receptor." J Biol Chem 272: 26991-26998 (1997).
McTarggart, "Isoprenylated Proteins," Cell. Mol Life Sci., 63, 255-267 (2006).

(Continued)

*Primary Examiner* — Rei-tsang Shiao
(74) *Attorney, Agent, or Firm* — Parks IP Law LLC; Collen A. Beard, Esq.

(57) ABSTRACT

Inhibitors of the enzyme prenylated methylated protein methyl esterase (PMPMEase), the last step in the prenylation process for many eukaryotic proteins, having the general structure $R_1$-X-A-B($R_2$)-Y or $R_1$-X-A($R_2$)-B-Y, where $R_1$ is preferably a polyisoprenyl group, X is a linking group, Y is a group that promotes affinity interactions to the active site of PMPMEase and imparts hydrolysis resistance to the inhibitor, A and B are bridge atoms, and $R_2$ is a characteristic-providing substituent.

5 Claims, 8 Drawing Sheets

OTHER PUBLICATIONS

Morris, et al, "Physiological Regulation of G Protein-Linked Signaling." Physiol Rev 79: 1373-1430 (1999).

Muhlig-Versen, et al, "Loss of Swiss Cheese/Neuropathy Target Esterase Activity Causes Disruption of Phosphatidylcholine Homeostasis and Neuronal and Glial Death in Adult Drosophila." J Neurosci 25: 2865-2873 (2005).

Muller-Vahl, et al, "Transient Severe Parkinsonism After Acute Organophosphate Poisoning." J Neurol Neurosurg Psychiatry 66: 253-254 (1999).

Myung, et al, "Role of Isoprenoid Lipids on the Heterotrimeric G Protein Gamma Subunit in Determining Effector Activation." J Biol Chem 274: 16595-16603 (1999).

Narayana, et al, "Synthesis of Some New 5-(2-Substituted-1,3-Thiazol-5-yl)-2-Hydroxy Benzamides and Their 2-Alkoxy Derivatives as Possible Antifungal Agents." Eur J Med Chem 39: 867-872 (2004).

Parish, et al, "Isoprenylation/Methylation of Proteins Enhances Membrane Association by a Hydrophobic Mechanism." Biochemistry 35: 8473-8477 (1996).

Pereira-Leal, et al., "Prenylation of Rab GTPases: Molecular Mechanisms and Involvements in Genetic Disease," FEBS Letters 498, 197-200 (2001).

Perez-Sala, et al, "Analogs of Farnesylcysteine Induce Apoptosis in HL-60 Cells." FEBS Lett 426: 319-324 (1998).

Perez-Sala, at al, "Prenylated Protein Methyltransferases do not Distinguish Between Farnesylated and Geranylgeranylated Substrates." Biochem J 284 (Pt 3): 835-840 (1992).

Regazzi, et al, "Prenylcysteine Analogs Mimicking the C-Terminus of GTP-Binding Proteins Stimulate Exocytosis from Permeabilized HIT-T15 Cells: Comparison with the Effect of Rab3AL Peptide." Biochim Biophys Acta 1268: 269-278 (1995).

Roskoski, Jr., "Protein Prenylation: A Pivotal Posttranslational Process," Biochemical and Biophysical Research Communications, 303 1-7 (2003).

Scheer, of al, "S-Prenylated Cysteine Analogues Inhibit Receptor-Mediated G Protein Activation in Native Human Granulocyte and Reconstituted Bovine Retinal Rod Outer Segment Membranes." Biochemistry 34: 4952-4961 (1995).

Seabra, et al., "Rab GTPases, Intercellular Traffic and Disease," Trends in Molecular Medicine, 8:1, 23-30 (2002).

Sebti, et al, "Anticancer Activity of Farnesyltransferase and Geranylgeranyltransferase I Inhibitors: Prospects for Drug Development." Expert Opin Investig Drugs 6: 1711-1714 (1997).

Seymour, "Novel Anti-Cancer Agents in Development: Exciting Prospects and New Challenges." Cancer Treat Rev 25: 301-312 (1999).

Shahar, et al, "Extrapyramidal Parkinsonism Complicating Acute Organophosphate Insecticide Poisoning." Pediatr Neurol 33: 378-382 (2005).

Shields, et al, "Understanding Ras: 'it ain't over 'til it's over'." Trends Cell Biol 10: 147-154 (2000).

Sinensky, "Functional Aspects of Polyisoprenoid Protein Substituents: Roles in Protein-Protein Interaction and Trafficking." Biochim Biophys Acta 1529: 203-209 (2000a).

Sinensky, et al, Recent Advances in the Study of Prenylated Proteins. Biochim Biophys Acta 1484: 93-106 2000b.

Winter-Vann, A Small-Molecule Inhibitor of Isoprenylcysteine CarboxylMethyt-transferase with Antitumor Activity in Cancer Cells, PNAS, 102:12, 4336-4341 (Mar. 22, 2005).

Chen, Yulong et al., "Solubilization, Partial Purification, and Affinity Labeling of the Membrane-Bound Isoprenylated Protein Endoprotease", Dept. of Biological Chemistry and Molecular Pharmacology, Harvard Medical School (Jan. 11, 1996).

* cited by examiner

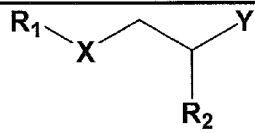

R₁ = Tail
X = Linking group
Bridge = Atoms between X and Y
Y = Ester, amide, sulfoxide, sulfone, sulfonate ester, sulfinate ester, sulfonamide, sulfinamide, phosphate ester, phosphonate ester, phosphinate ester, phosphoramide ester, phosphonamide, phosphinamide, thionphosphate ester, phosphonothioate ester, phosphinothioate ester, thionphosphate amide, phosphonothioate amide, phosphinothioate amide, (beta)-lactone , (beta)-lactam, chloromethyl ketone, propane dinitrile group
R₂ = Substituent may be an open chain alkyl, alicyclic, aryl, aryloxy and may contain one or more amino, carboxylic acid or hydroxyl functional goups, either separately or in combination. These may be on or be components of heterocycles such as piperazine, piperidine, pyrrolidine.

FIGURE 2

| Compound | Structure | Km (μM) | Vmax (nmol/s/mg) | Kcat (s⁻¹) | Kcat/Km (s⁻¹M⁻¹) |
|---|---|---|---|---|---|
| L-74 | 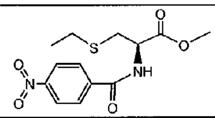 | 505 ± 63 | 477.6 ± 27 | 29.6 ± 1.7 | 58600 |
| L-77 | 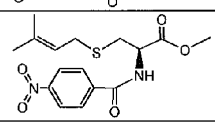 | 294 ± 25 | 199.1 ± 8.2 | 12.3 ± 0.51 | 41800 |
| L-72 | 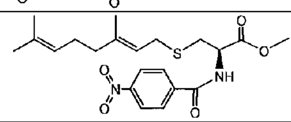 | 87 ± 12 | 62.8 ± 2.4 | 3.9 ± 0.15 | 45000 |
| RD-PNB | 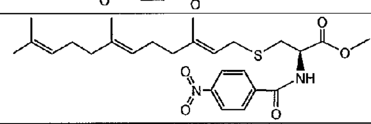 | 29 ± 2.2 | 5.3 ± 0.13 | 0.33 ± 0.01 | 11400 |
| L-80 | 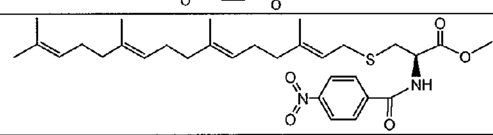 | 15 ± 2.7 | 0.74 ± 0.04 | 0.04 ± 0.002 | 2670 |

FIGURE 3

| Compound | Structure | Km (µM) | Vmax (nmol/s/mg) | Kcat (s⁻¹) | Kcat/Km (s⁻¹M⁻¹) |
|---|---|---|---|---|---|
| L-77 | 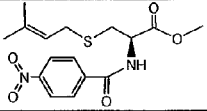 | 294 ± 25 | 199.1 ± 8.2 | 12.3 ± 0.51 | 41800 |
| L-81 | 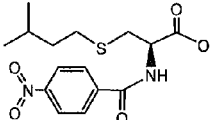 | 960 ± 180 | 373 ± 54 | 24.1 ± 3.4 | 25000 |
| L-72 | 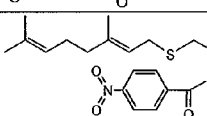 | 87 ± 12 | 62.8 ± 2.4 | 3.9 ± 0.15 | 45000 |
| L-83 | 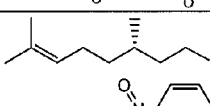 | 56 ± 9.6 | 47.4 ± 1.8 | 2.94 ± 0.11 | 52900 |
| L-86 | 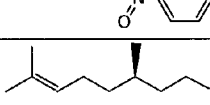 | 53 ± 7.0 | 47.3 ± 1.4 | 2.93 ± 0.09 | 55300 |
FIGURE 4

| Compound | Structure | Km (μM) | Vmax (nmol/s/mg) | Kcat (s⁻¹) | Kcat/Km (s⁻¹M⁻¹) |
|---|---|---|---|---|---|
| RD-PNB | 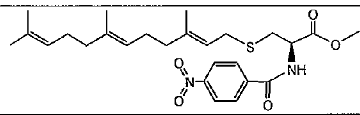 | 29 ± 2.2 | 5.3 ± 0.13 | 0.33 ± 0.01 | 11400 |
| L-70 | 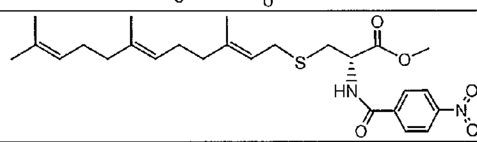 | 11 ± 0.9 | 0.93 ± 0.02 | 0.06 ± 0.001 | 5500 |

FIGURE 5

| Compound | Structure | Km (µM) | Vmax (nmol/s/mg) | Kcat (s⁻¹) | Kcat/Km (s⁻¹M⁻¹) |
|---|---|---|---|---|---|
| RD-PNB | 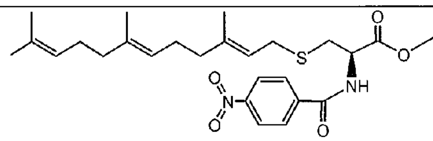 | 29 ± 2.2 | 5.3 ± 0.13 | 0.33 ± 0.01 | 11400 |
| L-76 | 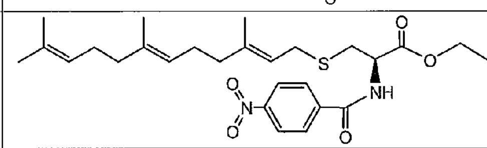 | 11 ± 0.89 | 7.4 ± 0.14 | 0.46 ± 0.01 | 41100 |
| L-75 | 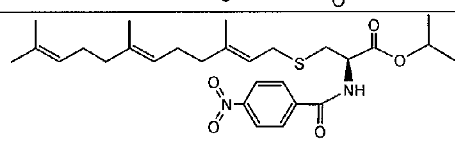 | 5.9 ± 0.66 | 2.6 ± 0.06 | 0.16 ± 0.004 | 27100 |

FIGURE 6

INHIBITORS OF POLYISOPRENYLATED METHYLATED PROTEIN METHYL ESTERASE

STATEMENT REGARDING FEDERALLY SPONSORED RESEARCH OR DEVELOPMENT

This research was supported in part by NIH/NIGMS/MBRS/SCORE grant GM 08111-35 and by Pharmaceutical Research Center NIH/NCRR grant G12 RR0 3020.

BACKGROUND OF THE INVENTION

The invention is in the field of inhibitors for the enzyme polyisoprenylated methylated protein methyl esterase (PMPMEase). The invention is also in the field of methods for medical treatment using inhibitors of the enzyme PMPMEase. The invention is further in the field of using PMPMEase inhibitors for diagnostic or clinical applications.

Protein polyisoprenylation and subsequent methylation are essential modifications on a significant proportion of eucaryotic proteins. The modifications are a series of post-translational modifications involving motifs such as —CAAX wherein C is cysteine, A is any aliphatic amino acid, and X is any amino acid. The modifications include polyisoprenylation of the cysteine of the —CAAX motif (on the sulfur), proteolysis of the carboxyl-terminal three amino acids (AAX), and methylation of the carboxyl group of the cysteine. In the polyisoprenylation step, a 15 carbon (trans,trans-farnesyl) or 20 carbon (all trans-geranylgeranyl) hydrocarbon group is covalently added to the protein. The prenylation pathway is shown in FIG. 1.

Proteins such as the G-gamma subunits of heterotrimeric G-proteins of the G-protein coupled receptors, nuclear lamins, and guanine nucleotide-binding proteins such as Ras are polyisoprenylated and undergo methylation. Polyisoprenylated proteins serve numerous functions in cells, including receptor signaling, vesicular trafficking, cell proliferation, differentiation and apoptosis.

The only reversible step in the process is the last step, methylation. Two enzymes mediate this final state of polyisoprenylated proteins. Polyisoprenylated protein methyl transferase (PPMTase), also known as isoprenyl carboxylmethyl transferase (ICMT), transfers a methyl group from S-adenosyl-L-methionine (SAM) to the C-terminal —COO$^-$ to form the methylated polyisoprenylated protein. PPMTase is essential to the developing embryo; knockout mice lacking PPMTase activity do not survive through mid-gestation. The second of the two enzymes, polyisoprenylated methylated protein methyl esterase (PMPMEase), hydrolyzes the methyl esters of polyisoprenylated proteins to form the original proteins with free —COO$^-$ groups.

PPMTase and PMPMEase counterbalance the effects of each other. It is conceivable that the methylated and demethylated forms of prenylated proteins may be variously preferred for functional interactions by different protein targets, thus rendering PPMTase and PMPMEase very important moderators of polyisoprenylated protein function. Accordingly, manipulation of these enzymes should render significant effects on many cellular functions.

U.S. Pat. No. 5,202,456 to Rando teaches compounds that inhibit the methylation step of the prenylation process. The compounds have the structure W-Y-Q-Z or W-Y-Z, where W is a farnesyl or geranylgeranyl group or substituted farnesyl or geranylgeranyl group, Y is certain sulfur and selenium moieties, Q is substituted hydrocarbon moieties, and Z is —COOH or salts or esters (preferably salts or esters (preferably methyl, ethyl, or propyl) thereof, —CN, or —SO$_3$ or salts or esters (preferably methyl, ethyl, or propyl) thereof.

U.S. Pat. No. 5,574,025 to Anthony teaches compounds which inhibit the prenylation of several proteins. The compounds are inhibitors of farnesyl-protein transferase and geranylgeranyl-protein transferase and are disclosed as being useful as chemotherapeutic agents.

U.S. Pat. No. 5,705,528 to Kloog teaches farnesyl derivatives which are inhibitors for prenylated protein methyltransferase enzyme (PPMTase). These compounds also are described as useful anti-cancer agents. Kloog hypothesized that focus on the reversible methylation step in the prenylation process would have less harmful effects than the use of inhibitors for the irreversible prenylation step itself.

U.S. Pat. No. 6,372,793 to Lamango et al. teaches compounds and methods for the treatment of neurological dysfunction. The compounds reverse an imbalance in methylation/demethylation of certain proteins. The compounds are prenyl cysteine compounds and analogs.

None of the above discussed prior art have focused on inhibitors for the enzyme that demethylates the prenylated protein, PMPMEase.

It is known that PMPMEase is inhibited by various organophosphorus compounds (OPs). This is interesting for a number of reasons. Parkinson's disease (PD)-like dyskinesias of a delayed nature have been reported following intoxication with OPs. It is known that OPs inhibition of an esterase known as neuropathy target esterase (NTE) is associated with organophosphate-induced delayed neuropathy (OPIDN). OPs inhibition of NTE in experimental animals causes the degeneration of long nerves towards the cell bodies.

It is known that excessive macromolecular carboxymethylation caused by intracerebroventricular injections of SAM results in PD-like effects of an analogous time profile. The SAM-induced PD-like effects are completely blocked by polyisoprenyl-L-cysteine (PC) analogs which are modeled around the C-terminal end of prenylated proteins.

Since PPMTase and PMPMEase act in reverse to each other, inhibition of PMPMEase and thus inhibition of the demethylation of prenylated proteins could have similar effects as this excessive methylation of prenylated proteins. PMPMEase inhibitors could be useful as research chemicals and could have clinical usefulness as antineoplastic agents.

PMPMEase, through its possible regulation of the functions of various types of polyisoprenylated proteins, may exert profound effects on various intracellular events and consequently on animal physiology. Putative substrates include both heterotrimeric guanine nucleotide-binding proteins (G-proteins), monomeric G-proteins, nuclear lamins, etc. These proteins mediate processes ranging from neurotransmitter signaling, cytoskeletal and intracellular transportation functions, cell proliferation, differentiation, and apoptosis. It could be inferred from this that aberrant levels of PMPMEase activity would be expressed through disease states such as cancers, neurodegenerative, and neuropsychiatric disorders.

SUMMARY OF THE INVENTION

PMPMEase inhibitors have been designed using the structures of known non-selective serine protease inhibitors and known substrates as guides. The general structure for the PMPMEase inhibitors of the invention is shown in FIG. 2. The inhibitors include a polyisoprenyl group, $R_1$, for specificity, and a Y group which promotes active site interaction but imparts resistance to hydrolysis by the enzyme. The inhibitors also include a linking group, X, and a two atom bridge between the X and Y groups. $R_2$ is a substituent that can be widely varied; $R_2$ generally corresponds to the polypeptide portion of endogenous protein substrates.

The compounds according to the invention are capable of inhibiting the demethylation of a methylated polyisoprenylated protein.

In a preferred embodiment, $R_1$ is trans,trans-farnesyl or all trans-geranylgeranyl; X is sulfur or selenium; the linking atoms are carbon; and Y is an ester, amide, sulfoxide, sulfone, sulfonate ester, sulfinate ester, sulfonamide, sulfinamide, phosphate ester, phosphonate ester, phosphinate ester, phosphoramide ester, phosphonamide, phosphinamide, thionphosphate ester, phosphonothioate ester, phosphinothioate ester, thionphosphate amide, phosphonothioate amide, phosphinothioate amide, (beta)-lactone, (beta)-lactam, chloromethyl ketone, or propane dinitrile group. One of the linking atoms preferably has a substituent to, for example, increase the aqueous solubility of the compounds.

The inhibitors can be used as experimental, diagnostic, and therapeutic reagents. Therapeutic formulations of the inhibitors include the inhibitor, or a pharmaceutically acceptable salt thereof, and a pharmaceutically acceptable carrier.

BRIEF DESCRIPTION OF THE DRAWINGS

FIG. 2 is a schematic of the general structure of PMPMEase inhibitors of the invention.

FIG. 3 is a table illustrating the effect of prenyl tail length on substrate affinity for PMPMEase.

FIG. 4 is a table illustrating the effect of prenyl tail saturation on substrate affinity for PMPMEase.

FIG. 5 illustrates the effect of the inhibitor $R_2$ group chirality on substrate affinity.

FIG. 6 demonstrates how various O-substituents increase affinity for PMPMEase.

DETAILED DESCRIPTION OF THE INVENTION

Figure 1:
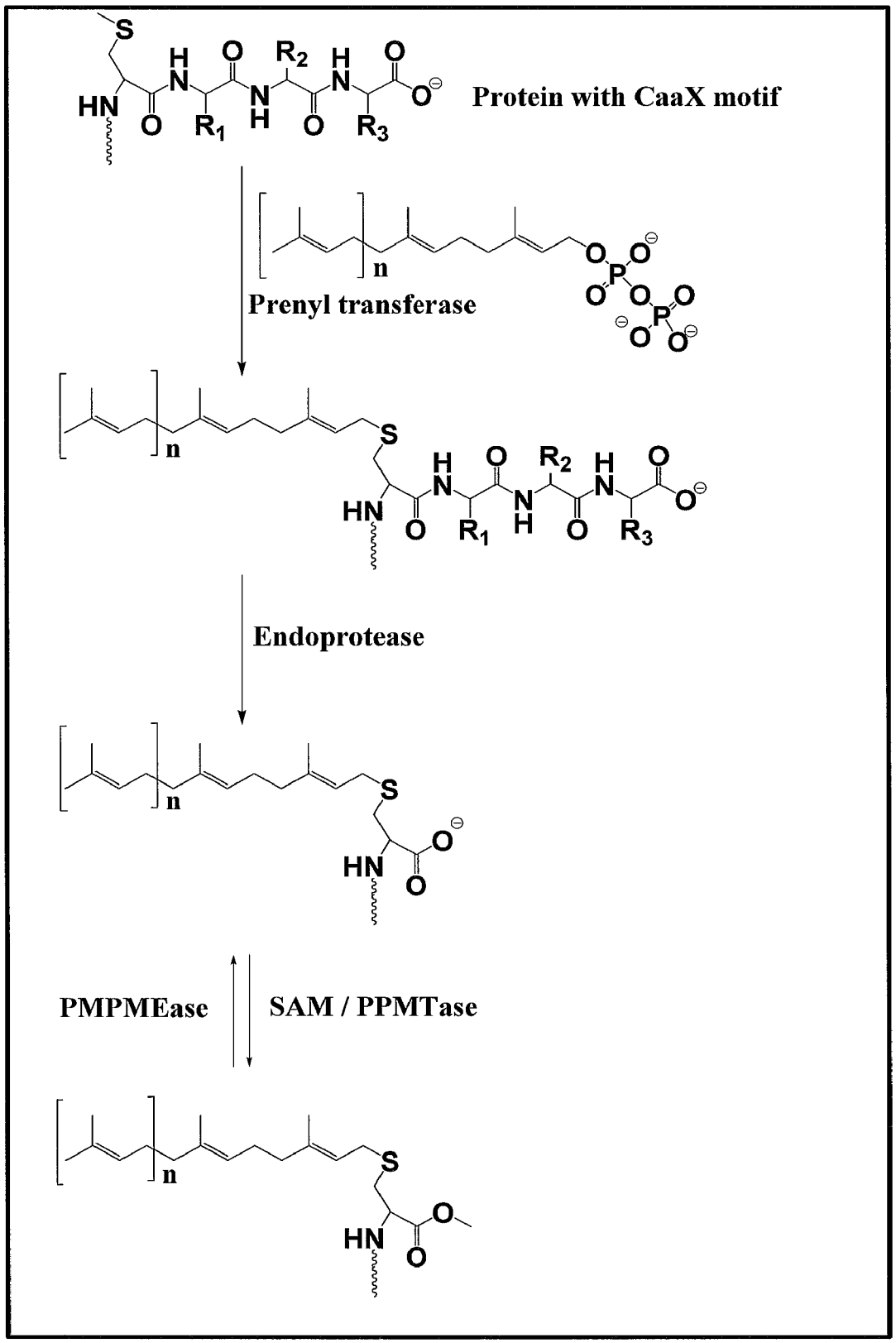
FIG. 1 is a schematic illustration of the prenylation pathway.

PMPMEase has been purified, sequenced and identified to be a serine hydrolase. As such, it has serine, histidine and glutamate residues at its active site that are involved in the catalytic process. During the hydrolysis of substrates, the histidine and glutamate residues combine to deprotonate the serine hydroxyl, creating a strong nucleophile that attacks the electron-deficient carbonyl carbon of the ester or amide substrates. The weakened ester bond breaks and while the alcohol product is released, the enzyme is temporarily acylated. Water is a strong enough nucleophile to rapidly reverse the acylation resulting in the release of the acid product and the fully recovered active enzyme.

Compounds in which the electron-deficient carbonyl carbon of the substrates is substituted with other electron-deficient atoms such as sulfur and phosphorus are attacked by the enzyme in a similar fashion. However, unlike the carboxylesters, these pseudo-substrates form covalent bonds with the enzyme that are not readily reversed by water and prevent the enzyme from binding to and hydrolyzing substrates as it normally would. Thus, these PMPMEase pseudo-substrates function as PMPMEase inhibitors. However, these pseudo-substrates without further modifications act non-selectively on all serine hydrolases, causing unwanted side effects if used as therapeutic agents.

PMPMEase inhibitors have been designed using the structures of known non-selective serine protease inhibitors and known substrates as guides. The PMPMEase inhibitors are, generally speaking, compounds having, on one end, a prenyl or polyisoprenyl group, and on the other end a group to impart active site interaction but hydrolysis-resistant. This group can be an ester, amide, sulfoxide, sulfone, sulfonate ester, sulfinate ester, sulfonamide, sulfinamide, phosphate ester, phosphonate ester, phosphinate ester, phosphoramide ester, phosphonamide, phosphinamide, thionphosphate ester, phosphonothioate ester, phosphinothioate ester, thionphosphate amide, phosphonothioate amide, phosphinothioate amide, (beta)-lactone, (beta)-lactam, chloromethyl ketone, or propane dinitrile group. The general structure for the PMPMEase inhibitors of the invention is shown in FIG. 2, where $R_1$ is the prenyl or polyisoprenyl group and Y is the active site reactant group. The inhibitors also include a linking group, X, and a bridge between the X and Y groups.

The Polyisoprenyl Group, $R_1$

The prenyl tail is important for ensuring the selectivity and affinity of the inhibitor towards PMPMEase. In polyisoprenylated proteins, $R_1$ is either a trans,trans-farnesyl moiety or an all trans-geranylgeranyl moiety. Thus the inhibitors are synthesized with prenyl or polyisoprenyl groups to render them more specific towards PMPMEase and so they have a low tendency to nonspecifically inhibit other enzymes. This is important for minimizing side effects. Using trans,trans-farnesyl or an all trans-geranylgeranyl as the $R_1$ substituent in inhibitors with pharmaceutical potential reduces the chances of undesired interactions with other proteins since these moieties are already substituents of proteins in the body.

FIG. 3 illustrates the results of varying the $R_1$ substituent on PMPMEase substrates. It was found that substrates with the trans,trans-farnesyl or an all trans-geranylgeranyl showed the highest affinity towards PMPMEase as revealed by the lower values for Km. The S-all trans-geranylgeranyl analog showed the highest affinity while the S-ethyl analog displayed the lowest affinity. From this, it can be concluded that in order to obtain high affinity inhibitors, the longer alkyl substituents will better serve this purpose. This does not however preclude the use of shorter chain substituents in the synthesis of the inhibitors. Although the trans,trans-farnesyl and all trans-geranylgeranyl moieties may be more effective with respect to selectivity and affinity, other groups such as alkyl, aryl, aryloxy, or substituted and unsubstituted prenyl, polyisoprenyl, alkyl, aryl, aryloxy, any of which can be saturated or unsaturated, may be used as the $R_1$ group.

Although $R_1$ bond saturation appears to decrease affinity as shown by higher Km values (FIG. 4) it does not prevent interactions with the enzyme. If such changes are incorporated in inhibitor design, high affinity inhibitors may still be obtained. Substitution of some hydrogen atoms for fluorine or chlorine should not drastically impact the inhibition.

Substrate analogs with $R_1$ S-phenyl or S-substituted phenyl are hydrolyzed by PMPMEase, indicating that similar S-substituents can be used in the inhibitors.

The Linking Group, X

The endogenous proteins that constitute the natural substrates of PMPMEase have sulfur as the linking group X. Substrates that have demonstrated a high affinity for PMPMEase also have sulfur as the linking group X. However other atoms or groups of atoms may also serve as the link between R$_1$ and the rest of the molecule in inhibitors of PMPMEase. For example, X can be S, Se, SO, SO$_2$, O, NH, NR (where R is —CN or alkyl), C(CN)$_2$ or CH$_2$.

The Bridge

In polyisoprenylated proteins, the bridge, which is the link between the sulfur atom and the carbonyl carbon is made up of two carbon atoms (CH$_2$CH). The importance of the link lies mainly in the distance it engenders between the polyisoprenyl tail and the carbonyl carbon of the substrates (or in the inhibitors, the Y group). This distance, which should be about 0.45 nm, ensures that while the polyisoprenyl tail binds effectively to its binding subsite on the enzyme active site, the carbonyl or the other electron-deficient atoms of the inhibitors (P, S, C bonded to electron-withdrawing atoms/groups) are able to interact with the electron-rich serine residue side chain. Shortening or lengthening this distance beyond certain limits, i.e., 1 or 3 atoms, will decrease the binding affinity of the inhibitors.

Other atoms such as nitrogen, oxygen or sulfur may be used in place of one of the carbon atoms. Any of the hydrogens of the bridging atoms may be substituted with F, Cl, alkyl or substituted alkyl or aryl structures as in the case of the substrates.

The Bridge can carry substituents, indicated by R$_2$. Since the R$_2$ substituent is replacing the polypeptide portion of an endogenous protein substrate, very diverse groups are envisioned and may be suitable for certain applications. In order to increase polarity and/or potency, it will be a substituent with an open chain alkyl, alicyclic, aryl, aryloxy and may contain one or more salt-forming basic or acidic groups such as amino, carboxylic acid, sulfonic, phosphoric or hydroxyl functional groups, either separately or in combination. These may be on or be components of heterocycles such as piperazine, piperidine, pyrrolidine. Other functional groups may be part of this substituent.

The R$_2$ group may contain a chiral center. Based on studies of PMPMEase substrates (FIG. 5), D-cysteine analogs show higher affinities (lower Km values) than the L-cysteine analogs. Although the L-cysteine analogs reflect what occurs in proteins, the substrate studies indicate that inhibitors with the D-cysteine may actually be more potent than the L-cysteine analogs. R$_2$ can vary enormously as would be predicted from the fact that the polypeptide chain of polyisoprenylated proteins represents R$_2$ in such protein substrates. The degree of tolerance in this part of the inhibitors is predicted from the substrates in which various substituents such as benzoic acid, para-nitrobenzoic acid, hippuric acid and hydrocinnamic acid have all been coupled to an amino substituent at the R$_2$ position. The substrates are not water soluble due to the fatty nature of the S-polyisoprenyl substituents that is compounded by the lack of polar groups in the molecule. For this reason, inhibitors can be synthesized with, for example, nitrogen-containing moieties such as piperazine, carboxyl-containing groups as well as alcohols. The polar groups impart aqueous solubility and increase affinity through electrostatic interactions or hydrogen bonding. To maximize any possible positive electrostatic interactions, a tether is required between the bridge and negatively or positively charged groups such as the carboxylate or quaternary ammonium salt species of the resulting compounds.

In polyisoprenylated proteins, the bridge is the branch point for connecting the polypeptide backbone of the polyisoprenylated protein. Given that the polypeptide backbone is analogous to a substituent on the Bridge of either inhibitors or substrates, the structural variability of R$_2$ is enormous. In designing inhibitors, such R$_2$ substituents will serve to impart physico-chemical flexibility such as for balancing aqueous/lipid solubility or other characteristics that are important for pharmaceutical formulations necessary for drug delivery to the target sites. Salt-forming substituents, through increased aqueous-solubility, will benefit the bioavailability of the otherwise hydrophobic molecules. Through possible electrostatic interactions with oppositely-charged groups on the enzyme, these substituents may also increase affinity and putative therapeutic effectiveness.

The Y Group

In polyisoprenylated methylated proteins, the carboxylmethyl ester group occupies the analogous position to that indicated by Y in FIG. 2. The general mechanism for serine esterase action indicates that during substrate hydrolysis, the electron deficient carbonyl carbon of the methyl ester interacts with the electron-rich catalytic serine residue side chain. While in the case of substrates this interaction is short-lived upon the formation of an acylated enzyme intermediate, changes in this susceptible portion of the molecule are used to increase the temporal extent of this interaction in the design of inhibitors. Inhibitors are obtained when the carbonyl/ester group is replaced in some cases by bioisosteres such as an ester, amide, sulfoxide, sulfone, sulfonate ester, sulfinate ester, sulfonamide, sulfinamide, phosphate ester, phosphonate ester, phosphinate ester, phosphoramide ester, phosphonamide, phosphinamide, thionphosphate ester, phosphonothioate ester, phosphinothioate ester, thionphosphate amide, phosphonothioate amide, phosphinothioate amide, (beta)-lactone, (beta)-lactam, chloromethyl ketone, propane dinitrile or hydroxyimino group. These may also be part of a cyclic structure as in lactones, lactams and their substituted analogs.

Tables 1 and 2 illustrate various compounds that inhibit PMPMEase, such as phenylmethylsulfonyl fluoride (PMSF), a large number of organophosphorus compounds (OPs), the diketone benzil, ebelactones, and chloromethylketones (CMK). These are mechanism-based inactivators because they mimic the substrate to a great extent except that the conversion of the enzyme-substrate intermediate to the enzyme and product is too slow and the enzyme is inhibited as a result. The compounds shown in Table 1 are very toxic, having been developed to serve as pesticides or nerve agents in chemical warfare. This toxicity is due in part to the fact that while they were designed to inhibit acetylcholinesterase, they also bind to and inhibit other enzymes such as PMPMEase.

Table 2 shows compounds with chloromethyl functional groups (—COCH$_2$Cl, CMK), lactones, PMSF, and the diketone benzil. Like the OPs, these react more or less irreversibly with serine hydrolases such as PMPMEase. However, because they have been designed to better target other serine hydrolases such as proteases and without the knowledge of PMPMEase substrates, their potency against PMPMEase is weak. These functional groups can be combined with the other structural elements as defined in FIG. 2 to target PMPMEase in order to achieve more potent inhibitors.

In one embodiment, Y can be

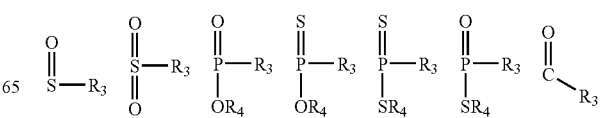

-continued

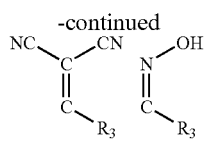

where $R_3$ is F, alkyl, substituted alkyl, aryl, substituted aryl, $SR_5$, $OR_5$, $NHR_5$, $NR_5R_6$, $CH_2$—Cl, $R_4$ is alkyl, substituted alkyl, aryl, or substituted aryl, and $R_5$ and $R_6$ are alkyl, substituted alkyl, aryl, or substituted aryl.

Where the Y group has two R groups attached, these may be distinct or combined in a cyclic or heterocyclic structure. Information from substrate kinetics analysis (FIG. 6) indicates that increasing the size from methyl (—$CH_3$) to ethyl (—$CH_2CH_3$) to isopropyl (—$CH(CH_3)_2$ increases the binding affinity as judged by the almost 5-fold decrease in Km between the O-methyl (RD-PNB) through O-ethyl (L-76) to the O-isopropyl (L-75) substrate analogs. The size of the $R_3$ and $R_4$ groups may be explored further to determine the nature and size that can produce optimal binding interactions with the enzyme.

The Y group and its subgroups $R_3$, $R_4$, $R_5$ and $R_6$ constitute a portion of the inhibitors that can be varied to distinguish between PMPMEase isoforms such as between brain and peripheral tissue forms of the enzyme. It is the nature of these groups that distinguish the types of OPs from each other with respect to the inhibition pattern against the brain and liver enzymes. Bulky substituents may be small enough to fit in the active site of one enzyme isoform but prevent access to the active site of another. Such subtleties are essential for ensuring selectivity in compounds that are used as therapeutic agents, in order to minimize side effects.

The term "alkyl" refers to a branched or straight chain unsaturated or saturated hydrocarbon group, having a carbon chain length of from 1 to 24 carbon atoms, such as methyl, ethyl, propyl, n-propyl, isopropyl, butyl, n-butyl, isobutyl, t-butyl, octyl, decyl, decyl, tetradecyl, hexadecyl, eicosyl, tetracosyl, cyclopentyl, cyclohexyl and the like. More particularly, the alkyl can be substituted or unsubstituted. When substituted, hydrogen atoms may be substituted with at least one member selected from the group consisting of CN, $NO_2$, S, NH, OH, COO—, and halogen at any available point of attachment. When the alkyl group is said to be substituted with an alkyl, this is used interchangeably with "branched alkyl" group.

The terms "cyclic" or "aryl" refer to aromatic rings, e.g. phenyl, substituted phenyl, benzene and the like as well as rings which are fused, e.g. naphthyl, phenanthrenyl, and the like. A cyclic or aryl group thus contains at least one ring having at least 6 atoms. Substituents on the cyclic or aryl group may be present on any position, i.e., ortho, beta, or para positions or fused to the aromatic ring. Suitable cyclic or aryl groups are phenyl, naphthyl and phenanthrenyl and the like. More particularly, cyclic or aryl groups may be unsubstituted or substituted with an aromatic or heteroaromatic group, and the aromatic or heteroaromatic group may be substituted with a substituent independently selected from the group consisting of a different aryl group, alkyl groups, halogens, fluoroalkyl groups; alkoxy groups, and amino groups. Preferred substituted aryl or cyclic groups include phenyl, naphthyl and the like.

The term "aryloxy" means an aryl group as defined above attached to a molecule by an oxygen atom (aryl-O) and includes, for example, phenoxy, naphthoxy and the like.

The term "alicyclic" is meant to describe nonaromatic ring compounds containing carbon and hydrogen atoms.

Methods of Using the Inhibitors

The present invention also relates to methods of using the PMPMEase inhibitors as therapeutic and diagnostic agents and to pharmaceutical formulations including the inhibitors. The inhibitors can be used in the diagnosis and treatment and/or prevention of cancers, and neuropsychiatric disorders. These diseases involve transmitter molecules that employ polyisoprenylated proteins and have in many cases of cancer been shown to have abnormal functioning of the polyisoprenylated proteins. The inhibitors can be used to further explore the functions and structure of PMPMEase.

The inhibitors can be used as reagents for specifically binding to PMPMEase and for aiding in PMPMEase isolation and purification or characterization. The inhibitors and purified enzyme can be used in screens for those individuals more genetically prone to develop certain cancers and neurodegenerative and neuropsychiatric disorders.

The present invention further provides a pharmaceutical formulation, for medicinal application, which comprises an inhibitor of the present invention or a pharmaceutically acceptable salt thereof, and a pharmaceutically acceptable carrier therefore.

The pharmaceutical formulations will typically be administered orally or by injection. Oral administration is preferred. Alternatively, other formulations can be used for delivery by pulmonary, mucosal or transdermal routes. The inhibitor will usually be administered in combination with a pharmaceutically acceptable carrier. Pharmaceutical carriers are known to those skilled in the art. The appropriate carrier will typically be selected based on the mode of administration. Pharmaceutical compositions may also include one or more active ingredients such as antimicrobial agents, anti-inflammatory agents, and analgesics.

Preparations for parenteral administration or administration by injection include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Preferred parenteral vehicles include sodium chloride solution, Ringer's dextrose, dextrose and sodium chloride, lactated Ringer's, or fixed oils. Intravenous vehicles include fluid and nutrient replenishers, and electrolyte replenishers (such as those based on Ringer's dextrose).

Formulations for topical (including application to a mucosal surface, including the mouth, pulmonary, nasal, vaginal or rectal) administration may include ointments, lotions, creams, gels, drops, suppositories, sprays, liquids and powders. Formulations for these applications are known. For example, a number of pulmonary formulations have been developed, typically using spray drying to formulate a powder having particles with an aerodynamic diameter of between one and three microns, consisting of drug or drug in combination with polymer and/or surfactant.

Compositions for oral administration include powders or granules, suspensions or solutions in water or non-aqueous media, capsules, sachets, or tablets. Thickeners, flavorings, diluents, emulsifiers, dispersing aids or binders may be desirable. Dosing is dependent on severity and responsiveness of the condition to be treated, but will normally be one or more doses per day, with course of treatment lasting from several days to several months or until the attending physician determines no further benefit will be obtained. Persons of ordinary skill can determine optimum dosages, dosing methodologies and repetition rates.

The formulations may be prepared by any of the methods well known in the art of pharmacy. All methods include the step of bringing into association the active ingredient, i.e., the compound or salt of the present invention, with the carrier. In general, the formulations are prepared by uniformly and intimately bringing into association the active ingredient with a liquid carrier or, a finely divided solid carrier or both, and then, if necessary, forming the associated mixture into the desired formulation.

The pharmaceutical formulations of the present invention suitable for oral administration may be presented as discrete units, such as a capsule, cachet, tablet, or lozenge, each containing a predetermined amount of the active ingredient; as a powder or granules; as a solution or a suspension in an aqueous liquid or a non-aqueous liquid such as a syrup, elixir or a draught, or as an oil-in-water liquid emulsion or a water-in-oil liquid emulsion. The formulation may also be a bolus, electuary or paste.

The examples below serve to further illustrate the invention, to provide those of ordinary skill in the art with a complete disclosure and description of how the compounds, compositions, articles, devices, and/or methods claimed herein are made and evaluated, and are not intended to limit the scope of the invention. In the examples, unless expressly stated otherwise, amounts and percentages are by weight, temperature is in degrees Celsius or is at ambient temperature, and pressure is at or near atmospheric.

A representative example of chemical structures (1-67) illustrates the inhibition of brain vs. liver PMPMEase with various organophosphorus compounds, and the selectivity of OPs for brain vs. liver PMPMEase is shown below in Table 1.

TABLE 1

| No | Name | Structure | Brain Mean | Brain SEM | Liver Mean | Liver SEM |
|---|---|---|---|---|---|---|
| 1 | Abate | | 59 | 4.6 | 80 | 1.4 |
| 2 | Azinphos-M | | 73 | 4.9 | 47 | 0.1 |
| 3 | Acephate | | 50 | 7.6 | NO INHIBITION | |
| 4 | Bensulide | | 82 | 3.1 | 76 | 2.3 |
| 5 | Bromophos-E | | 68 | 0.4 | 76 | 1.8 |
| 6 | Carbophenothion | | 55 | 3.7 | 49 | 1.1 |
| 7 | Chlormefos | | 65 | 1.9 | 86 | 7.2 |
| 8 | Chlorpyriphos | | 67 | 4.9 | 100 | 0.0 |

TABLE 1-continued

| No | Name | Structure | Brain Mean | Brain SEM | Liver Mean | Liver SEM |
|----|------|-----------|------------|-----------|------------|-----------|
| 9 | Chlorphoxim | 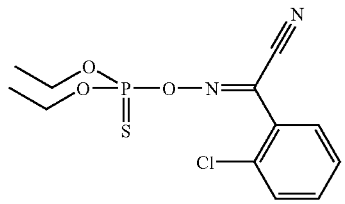 | 55 | 1.5 | 100 | 0.0 |
| 10 | Chlorthiophos | 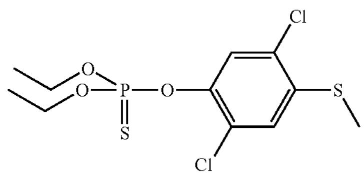 | 22 | 1.3 | 52 | 0.7 |
| 11 | Coumaphos | 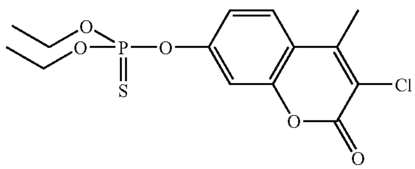 | 62 | 0.6 | 46 | 0.9 |
| 12 | Cyamophenphos | 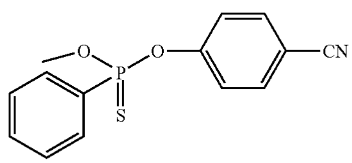 | 52 | 0.9 | 53 | 1.1 |
| 13 | Cyanophos | 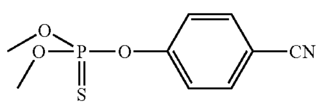 | 65 | 2.0 | 89 | 0.2 |
| 14 | Demeton-S-M | 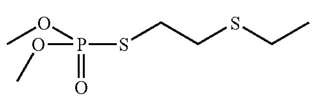 | 31 | 1.5 | 12 | 0.7 |
| 15 | Demeton-S | 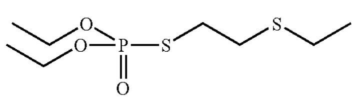 | 62 | 4.2 | 96 | 0.2 |
| 16 | Diazinon | 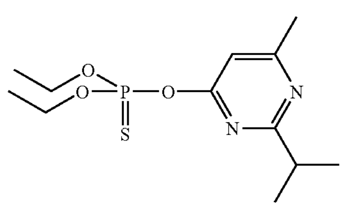 | 31 | 0.1 | 95 | 0.1 |
| 17 | Dialifos | 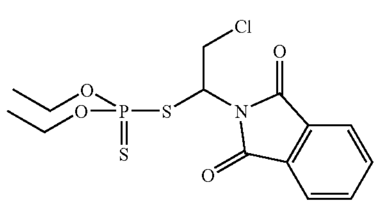 | 52 | 0.3 | 96 | 0.2 |

TABLE 1-continued

| No | Name | Structure | Brain Mean | Brain SEM | Liver Mean | Liver SEM |
|----|------|-----------|------------|-----------|------------|-----------|
| 18 | Dibrom | 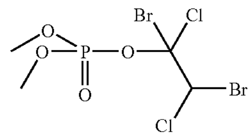 | 41 | 2.3 | 82 | 4.9 |
| 19 | Dichlofenthion | 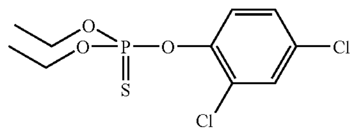 | NO INHIBITION | | 56 | 0.9 |
| 20 | Dichlorvos | 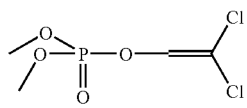 | 81 | 1.0 | 83 | 13.6 |
| 21 | Dicrotophos | 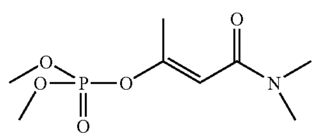 | N/A | | 56 | 1.07 |
| 22 | Dimefox | 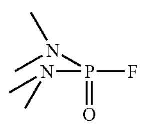 | N/A | | 13 | 0.58 |
| 23 | Dimethoate | 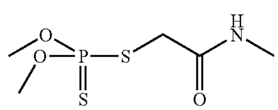 | N/A | | 12 | 0.72 |
| 24 | Dioxathion | 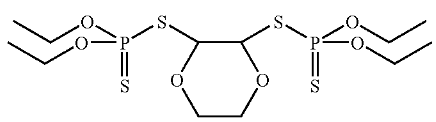 | 15 | 6.6 | 57 | 0.9 |
| 25 | Disulfoton | 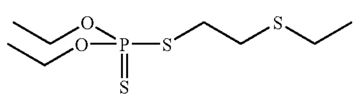 | NO INHIBITION | | 38 | 2.7 |
| 26 | Edifenphos | 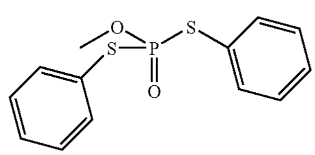 | 81 | 1.0 | 97 | 0.3 |
| 27 | Ethion | 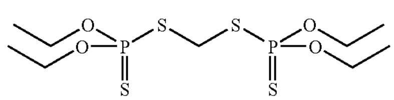 | NO INHIBITION | | 92 | 0.3 |
| 28 | Famphur | 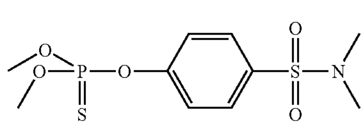 | 60 | 0.1 | 71 | 0.9 |
| 29 | Fenitrothion | 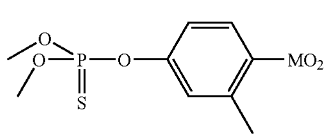 | 75 | 2.5 | 98 | 0.5 |

TABLE 1-continued

| No | Name | Structure | Brain Mean | Brain SEM | Liver Mean | Liver SEM |
|----|------|-----------|------------|-----------|------------|-----------|
| 30 | Fensulfothion | | 100 | 0.0 | 100 | 0.0 |
| 31 | Fenthion | | 17 | 1.1 | 40 | 0.5 |
| 32 | Fonofos | | 100 | 0.0 | 66 | 1.0 |
| 33 | Heptenophos | | 71 | 0.9 | 96 | 0.1 |
| 34 | Jodfenphos | | 69 | 0.2 | 96 | 0.0 |
| 35 | Leptophos | | 29 | 1.4 | 60 | 1.4 |
| 36 | Malaoxon | | 51 | 0.4 | 87 | 0.1 |
| 37 | Malathion | | 51 | 1.0 | 53 | 0.7 |
| 38 | Methyl-Parathion | | 75 | 0.9 | 100 | 0.0 |
| 39 | Mephosfolan | | N/A | | 100 | 0.0 |

TABLE 1-continued

| No | Name | Structure | Brain Mean | Brain SEM | Liver Mean | Liver SEM |
|----|------|-----------|------------|-----------|------------|-----------|
| 40 | Methacrifos | 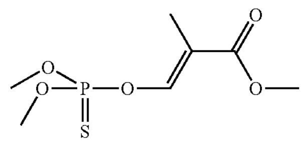 | 61 | 1.7 | 87 | 0.1 |
| 41 | Methamidophos | 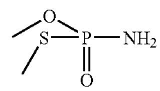 | 24 | 1.3 | 45 | 0.1 |
| 42 | Methidathion | 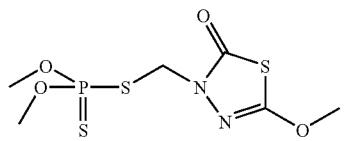 | 56 | 0.0 | 78 | 0.3 |
| 43 | Mipafox | 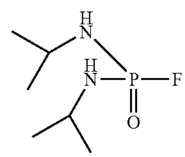 | 40 | 1.2 | 94 | 0.1 |
| 44 | Monocrotophos | 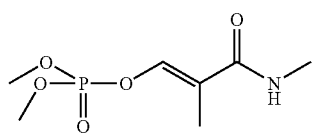 | 30 | 0.5 | 18 | 2.5 |
| 45 | Omethoate | 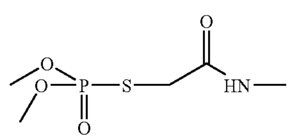 | 33 | 1.7 | 12 | 0.4 |
| 46 | Phenamiphos | 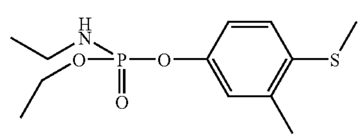 | N/A | | 92 | 0.5 |
| 47 | Phenthoate | 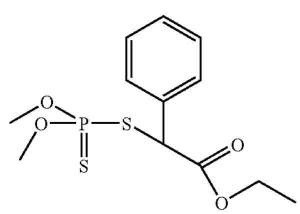 | 55 | 0.6 | 96 | 0.2 |
| 48 | Phosalone | 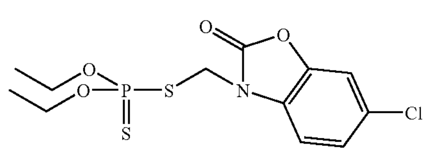 | 62 | 2.1 | 79 | 0.3 |
| 49 | Phosphamidon | 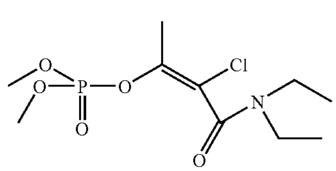 | 53 | 2.4 | 69 | 0.9 |

TABLE 1-continued

| No | Name | Structure | Brain Mean | Brain SEM | Liver Mean | Liver SEM |
|---|---|---|---|---|---|---|
| 50 | Pirimiphos-M | 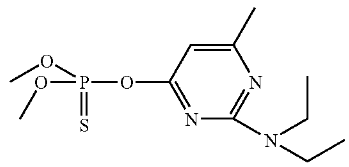 | 42 | 1.2 | 79 | 0.4 |
| 51 | Profenofos | 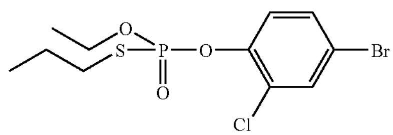 | 81 | 0.5 | 97 | 0.3 |
| 52 | Phosdrin | 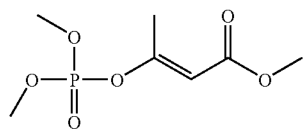 | 67 | 2.1 | 70 | 0.5 |
| 53 | Prophos | 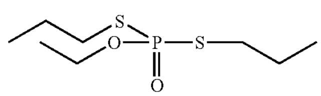 | 47 | 1.1 | 94 | 0.2 |
| 54 | Prothiofos | 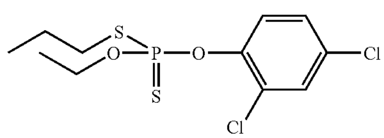 | 6 | 0.8 | 52 | 0.3 |
| 55 | Pyraclofos | 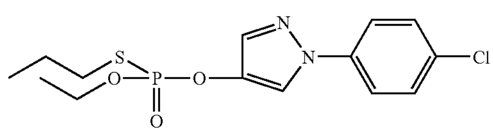 | 82 | 0.6 | 95 | 0.1 |
| 56 | Ronnel | 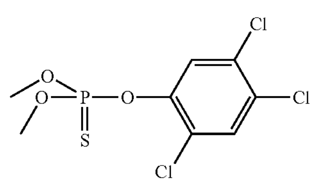 | 45 | 1.2 | 93 | 0.2 |
| 57 | Safrotin | 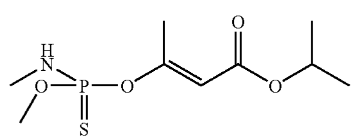 | 52 | 6.0 | 54 | 2.3 |
| 58 | Sulfotep | 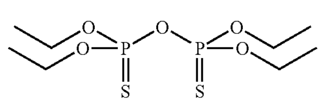 | 47 | 1.6 | 97 | 0.0 |
| 59 | Terbufos | 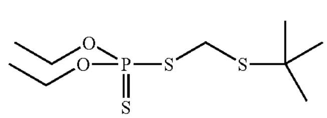 | 100 | | 72 | 0.9 |

TABLE 1-continued

| No | Name | Structure | Brain Mean | Brain SEM | Liver Mean | Liver SEM |
|---|---|---|---|---|---|---|
| 60 | Tetrachlorvinphos | 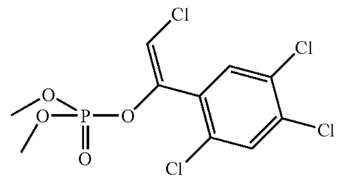 | 100 | | 91 | 0.4 |
| 61 | Triazophos | 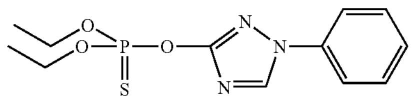 | 100 | | 100 | 0.0 |
| 62 | Trichlorfon | 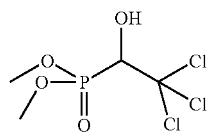 | 100 | | 91 | 0.4 |
| 63 | Tokuthion | 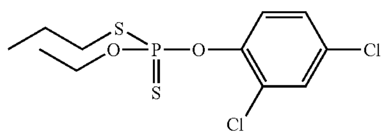 | 100 | | 76 | 0.7 |
| 64 | Vamidothion | 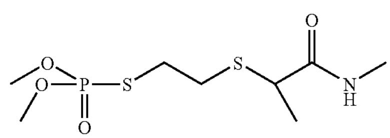 | N/A | | 55 | 11.3 |
| 65 | Zinophos | 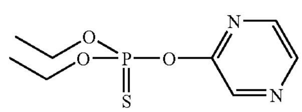 | N/A | | 96 | 0.1 |
| 66 | Etrimfos | 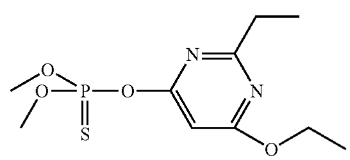 | 78 | 1.57 | 100 | 0.0 |
| 67 | Paraoxon | 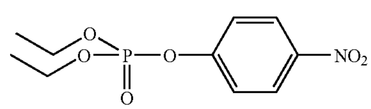 | 87 | 1.4 | 100 | 0.0 |

A representative example of chemical structures (1-12) illustrates various non-OP serine-hydrolase inhibitors which also inhibit PMPMEase is shown below in Table 2.

TABLE 2

| Compounds tested | Structure | Residual activity (% of Control, SEM, n = 3) | |
|---|---|---|---|
| | | 1 mM | 0.1*/0.01 mM |
| 1 Asulam | | 91.7 ± 6.9 | 113 ± 6.3 |

TABLE 2-continued

| Compounds tested | Structure | Residual activity (% of Control, SEM, n = 3) | |
|---|---|---|---|
| | | 1 mM | 0.1*/0.01 mM |
| 2 Benzil | | 38.0 ± .43 | *69.4 ± 0.24 |
| 3 Benzyl carbamate | | 124 ± 5 | 117 ± 11 |
| 4 Ebelactone A | | 18.3 ± 0.3 | 123 ± 7 |
| 5 Ebelactone B | | 0 ± 0 | 56.4 ± 1.0 |
| 6 L-Leu chloromethyl ketone (CMK) | | 60.4 ± 1.9 | 93.3 ± 1.0 |
| 7 N-carbobenzyloxy-L-Phe CMK | | 57.0 ± 2.0 | 94.8 ± 1.3 |
| 8 N-(methoxysuccinyl)-L-Ala-L-Ala-L-Pro-L-Val CMK | | 61.8 ± 2.0 | 105 ± 3.1 |
| 9 Nα-tosyl-L-Lys CMK | | 98.6 ± 7.3 | 98.3 ± 1.9 |
| 10 N-p-tosyl-L-Phe CMK | | 13.9 ± 1.1 | 96.5 ± 1.4 |

TABLE 2-continued

| Compounds tested | Structure | Residual activity (% of Control, SEM, n = 3) | |
|---|---|---|---|
| | | 1 mM | 0.1*/0.01 mM |
| 11 Paraoxon | 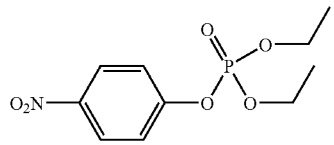 | 0 ± 0 | 0 ± 0 |
| 12 Phenylmethylsulfonyl fluoride | 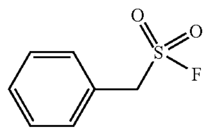 | 0 ± 0 | 79.5 ± 1.8 |

EXAMPLES

Materials

Porcine liver was obtained from Bradley's Country Stores, Tallahassee, Fla. within one hour of slaughter and frozen until required for enzyme preparation. Porcine heads were obtained from the same source within an hour of slaughter. Diethylaminoethyl (DEAE) Sepharose, Phenyl Sepharose, Chelating Sepharose, Cibacron Blue Sepharose, trans,trans-farnesol, benzil and hydrocinnamoyl chloride, organophosphorus compounds, benzil, various chloromethyl ketones, carbamates, ebelactones A and B, and PMSF were purchased from Sigma-Aldrich (St. Louis, Mo.). SDS-PAGE gels were from Fisher Scientific (Suwannee, Ga.).

Synthesis of Hydrocinnamoyl-farnesyl-L-Cysteine Methyl ester

Farnesyl-L-Cysteine methyl ester (FCM) was synthesized as described in Ma et al., *Methods Enzymol.* 250, 226-34 (1995). The FCM (1 g) was dissolved in approximately 100 ml of acetone followed by the addition of triethylamine (TEA, 1 ml) and 1 g of hydrocinnamoyl chloride. This was stirred for 2 h at room temperature. The solvent was removed under reduced pressure, the residue dissolved in 150 ml of ethylacetate and washed three times with water. The ethylacetate layer was dried with anhydrous sodium sulfate, filtered and the ethylacetate removed under reduced pressure. The residue was purified by silica gel chromatography to obtain hydrocinnamoyl-farnesyl-L-Cysteine methyl ester (HCFCM). The purified HCFCM was then analyzed by Electron Spray Ionization Mass Spectrometry (ESI-MS).

Enzyme Preparation and Assay

For liver enzyme, the supernatant fraction was prepared from 100 g of porcine liver as described in Lamango, *J Biochem Mol Toxicol* 19, 347-57 (2005). For brain enzyme, the brains were removed from the heads and cleaned of blood clots. Brain membranes were then prepared and extracted with 1% Triton X-100 as previously described (Lamango 2005). The Triton X-100 membrane extract was supplemented with 10% glycerol, aliquoted and frozen for subsequent use. Assay for PMPMEase activity was conducted using 1 mM of either BzGFCM or HCFCM substrate as described in Lamango 2005. The supernatant was kept on ice and used for the purification of PMPMEase.

PMPMEase Purification

PMPMEase was purified as described in Oboh and Lamango, *J Biochem Mol Toxicol* 22, 51-62 (2008) from porcine liver supernatant. Ice-cold porcine liver supernatant (8.8 g of protein in 1000 ml) was loaded onto a diethylaminoethyl (DEAE, 4.8 I.D.×60 cm) ion-exchange column that had previously been equilibrated with 20 mM Tris-HCl (pH 7.4) containing 0.1% Triton X-100 (Buffer A) at a flow rate of 5 ml/min. This was followed by washing with Buffer A until the UV absorbance at 280 nm subsided to the preloading values. The bound enzyme was then eluted from the column using a linear gradient from 0 to 1 M NaCl in Buffer A over 2 hours. Fractions (4.5 ml) were collected and aliquots assayed for enzyme activity using HCFCM as substrate. Fractions with enzymatic activity (Fractions 121-310) were combined and subjected to further purification by hydrophobic interaction chromatography (HIC) on a column of Phenyl Sepharose. The pooled fractions from the DEAE column were supplemented with NaCl to a concentration of 1 M and then loaded at a flow rate of 1.5 ml/min onto the HIC column (2.5 cm I.D.×30 cm) that had been pre-equilibrated with Buffer A containing 1 M NaCl. After loading, the column was washed with the same buffer and the enzyme eluted with a linear gradient from 1 to 0 M NaCl in the same buffer. Fractions (4.5 ml) were collected and aliquots of the fractions analyzed for enzyme activity. The fractions with enzymatic activity were combined and subjected to further purification on $Ni^{2+}$-charged immobilized metal ion affinity chromatography (Ni-IMAC). The chelating resin was charged with $Ni^{2+}$ ions and equilibrated with Buffer A. The pooled enzyme containing fractions from the HIC step were applied to the Ni-IMAC column at a flow rate of 0.5 ml/min and washed with Buffer A. Elution was conducted with an increasing gradient of histidine from 0 to 50 mM in the same buffer. Aliquots of the 4.5 ml fractions were assayed for PMPMEase activity. The combined active fractions were further purified on a Q-Sepharose column (1 cm I.D.×15 cm). The binding and elution was conducted with the same buffers as in the DEAE purification step except that the required volumes were significantly less. Fractions (4.5 ml) were collected and aliquots assayed for enzyme activity. Fractions with enzyme activity were combined and subjected to gel filtration chromatography on a Superdex 200 column (2 cm I.D.×90 cm) that was pre-equilibrated and eluted with Buffer A at a flow rate of 2.5 ml/min. Enzyme-containing fractions were further purified by Cu-IMAC, loading and washing in Buffer A and eluting with a 0 to 50 mM gradient of histidine in Buffer A. The fractions containing PMPMEase activity were combined and applied onto a Cibacron Blue 3GA column (1 cm I.D.×15 cm) that had been pre-equilibrated with Buffer A. The flow-through contained virtually all of the PMPMEase enzymatic activity.

PMPMEase bound to the different chromatographic media and was successfully eluted according to the procedures above. The enzyme did not bind to the Cibacron Blue that was used in the last chromatographic step. The Cibacron Blue did however appear to bind to some of the contaminating proteins as the enzyme flowed through. As shown in Table 3, the specific activity increased from 0.4 to 5.29 nmol of HCFCM hydrolyzed per min per mg of protein. This coincided with an over 13-fold enrichment of the PMPMEase activity. Over 80% of the enzyme activity was lost during the first purification step that involved ion-exchange on DEAE Sepharose (Table 3). SDS-PAGE protein analysis of samples from the different chromatographic steps revealed a successive elimination of contaminating protein bands that culminated in a single band of 57 kDa observed in the unbound fraction from the Cibacron Blue step. This shows that although the enzyme did not bind to the Cibacron Blue medium, it did indeed trap the remaining contaminating proteins from the Cu-IMAC column.

TABLE 3

Purification of porcine liver PMPMEase

| Chromatographic step | Total activity (nmol/min) | Total protein (mg) | Specific activity (nmol/min/mg) | Purification factor | Yield (%) |
| --- | --- | --- | --- | --- | --- |
| Supernatant | 3485 | 8805 | 0.40 | 1 | |
| DEAE | 704 | 3113 | 0.23 | 0.57 | 20 |
| HIC | 667 | 484 | 1.38 | 3.48 | 19 |
| Ni-IMAC | 374* | 265 | 1.41 | 3.57 | 11 |
| Q-Sepharose | 444 | 220 | 2.02 | 5.09 | 13 |
| Gel-filtration | 221 | 75 | 2.96 | 7.47 | 6 |
| Cu-IMAC | 150 | 60 | 2.49 | 6.28 | 4 |
| Cibacron blue | 127 | 24 | 5.29 | 13.23 | 3.6 |

Protein Assays

The total protein concentration in various samples was measured using the BCA Protein Assay Reagent kit (Pierce) according to the supplier's procedures. Bovine serum albumin was used as the standard.

SDS-PAGE Analysis

Aliquots (50 µl) of all protein samples were combined with 50 ul of SDS-PAGE sample buffer and boiled for 5 min. The samples were then separated on 4-12% gradient gels and the protein bands visualized by EZBlue coomassie staining (Sigma Chemical Co., St. Louis Mo.). SDS-PAGE molecular weight markers were used to calculate the molecular weight of the purified protein.

Protein Sequence Analysis

Purified PMPMEase was subjected to protein sequence analysis as described in Oboh and Lamango 2008.

Inhibition of Brain and Liver PMPMEase by OPs

Porcine liver 40,000×g supernatant (19 µg protein) or brain membrane Triton X-100 extract (47 µg protein) was incubated with a PC analog substrate of PMPMEase at 37° C. either in the absence (controls) or presence of 1 mM concentrations of the indicated OP for 1 h (liver supernatant) or 3 h (brain membrane Triton X-100 extract). Reactions were stopped and analyzed as previously described (Lamango 2005). The results are the mean percent inhibition relative to the controls±SEM, N=3. Results are shown in Table 1.

Inhibition of Purified PMPMEase by Serine-Hydrolase Inhibitors

Purified PMPMEase (10 µg) was incubated with 1, 0.1 (benzil only) and 0.01 mM concentrations of the indicated compounds for 20 min at 37° C. HCFCM (1 mM) was then added followed by further incubation and HPLC analysis. The results represent the residual activity expressed as percentages of the control (mean±S.E.M., n=3); the most inhibitory compounds showing 0% residual activity for the respective concentrations. The results are shown in Table 2.

Inhibitor Synthesis and Assays

Figure 7:
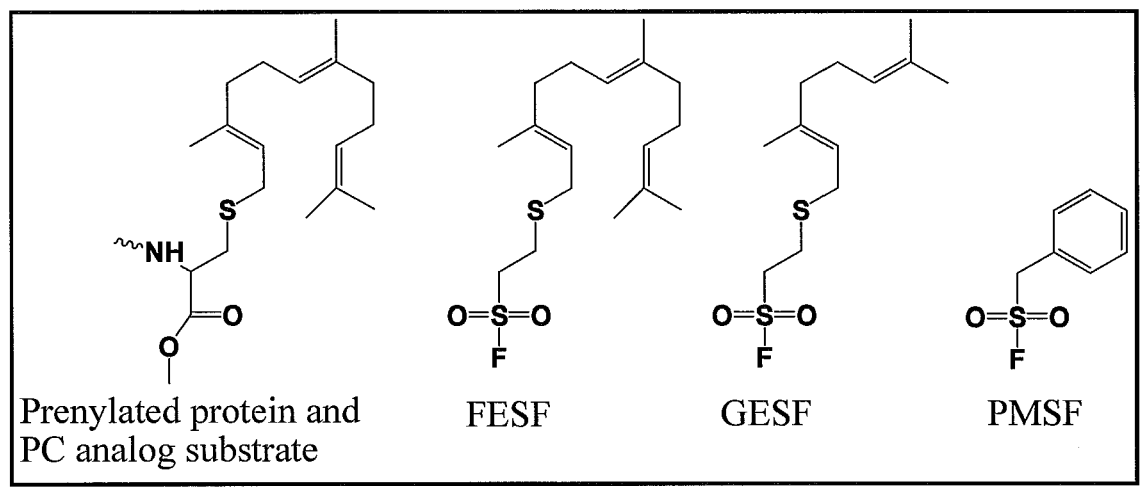
FIG. 7 is a schematic of the structures of the PMPMEase inhibitors S-farnesyl-2-thioethanesulfonyl fluoride (FESF), S-geranyl-2-thioethanesulfonyl fluoride (GESF) and phenylmethylsulfonyl fluoride (PMSF).

Two PMPMEase inhibitors were synthesized, based on manipulating the structure of the known non-specific inhibitor phenylmethylsulfonyl fluoride (PMSF). The structures of a prenylated protein (substrate), S-trans,trans-farnesyl-2-thioethanesulfonyl fluoride (FESF), S-trans-geranyl-2-thioethanesulfonyl fluoride (GESF), and PMSF are shown in FIG. 7. The main differences between the substrate and the inhibitors are the replacement of the carboxylester of the substrate with sulfonyl fluoride; and the presence and size of the prenyl groups.

Synthesis of S-trans-geranyl-2-thioethanesulfonyl fluoride (GESF) and S-trans,trans-farnesyl-2-thioethanesulfonyl fluoride (FESF)

trans-geraniol and trans,trans-farnesol were reacted with phosphorus tribromide to convert them to the corresponding according to previously published method for the synthesis of all trans-geranylgeraniol (Giner, J.-L. and Rando, R. R., *Biochemistry* 33, 15116-15123 (1994)). The corresponding bromides were reacted with thiourea in dry isopropanol to form the corresponding isothiouronium bromides. After extraction and drying, these were then refluxed with sodium hydroxide for 1.5 hours. They were allowed to cool and were extracted at pH 4 with hexane. The hexane extracts were dried over magnesium sulfate and the hexane evaporated. Vinylsulfonyl fluoride was prepared from 2-chlorosulfonyl chloride and potassium fluoride and water. The trans-geranylthiol and trans,trans-farnesylthiol were each reacted with vinylsulfonyl fluoride in the presence of 1 M tetrabutylammonium fluoride in tetrahydrofuran for 20 h. The tetrahydrofuran was removed and the resulting compounds, S-trans-geranyl-2-thioethanesulfonyl fluoride (GESF) and S-trans,trans-farnesyl-2-thioethanesulfonyl fluoride (FESF) were distilled from the respective residues under vacuum (Lamango, N. S. and Koikov, L N, unpublished).

Assays

Assays were conducted as generally described in Oboh and Lamango 2008. PMSF, GESF and FESF were each dissolved in DMSO and aliquots were incubated with porcine liver PMPMEase in 100 mM Tris/HCl buffer, pH 7.4 for 15 min. Substrate (BzGFCM, 1 mM) was then added followed by further incubation and analysis as described in the "Enzyme preparation and assay" section. Because GESF and FESF are not aqueous-soluble, analogs with polar substituents on the ethane portion of the molecules ($R_2$ in FIG. 2) will be more amenable to formulation, bioavailability and possibly higher inhibitory potency/therapeutic effectiveness.

Results

Figure 8:
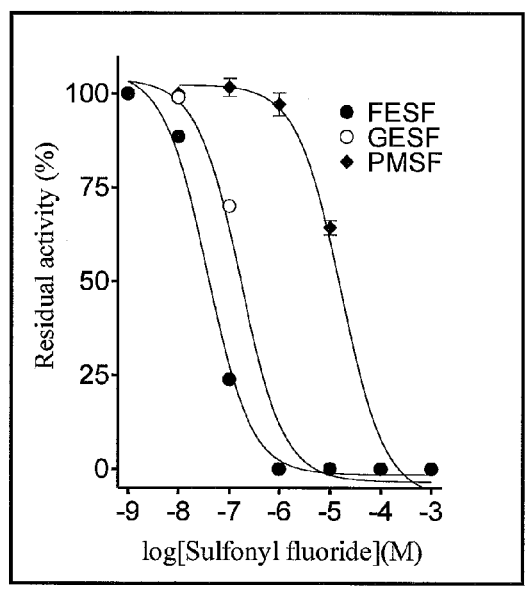
FIG. 8 compares the inhibition of porcine liver supernatant PMPMEase hydrolysis of HCFCM by S-farnesyl-2-thioethanesulfonyl fluoride (FESF), S-geranyl-2-thioethanesulfonyl fluoride (GESF) and phenylmethylsulfonyl fluoride (PMSF).

The results are shown in FIG. 8. Potency of PMPMEase inhibition (as judged by $IC_{50}$ values) increased from PMSF (16,400±640 nM) through GESF (169±6.8 nM) to FESF (37±0.42 nM). This reflects an increase in potency of over 97- and 440-fold for GESF and FESF, respectively. It is concluded from the data that the corresponding S-geranylgeranyl sulfonyl fluoride (GGESF) would display a 2-fold higher potency than FESF. Of all potential inhibitors, the geranylgeranylated forms would be most potent.

In addition to the increased potency of the inhibitors, another advantage is that the S-polyisoprene structure of FESF should target the compounds to PMPMEase and away from other enzymes because they mirror the specificity of the polyisoprenylated proteins themselves.

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. A method of inhibiting PMPMEase in a patient, comprising administering to the individual an effective amount of an inhibitor of PMPMEase, wherein the inhibitor has the formula:

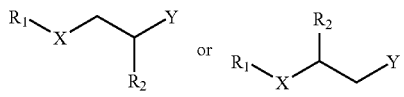

where $R_1$ is a group selected from substituted or unsubstituted prenyl or polyisoprenyl;

X is a linking group;

the two atoms between the X and Y groups are the bridge and are two carbon atoms or nitrogen, oxygen, or sulfur may be used in place of one of the carbon atoms;

$R_2$ is a group substituted with an open chain alkyl, alicyclic, aryl, or aryloxy group containing one or more salt-forming basic or acidic groups, either separately or in combination which may be on or be components of heterocycles selected from piperizine, piperidine, and pyrrolidine and $R_2$ is separated from the bridge by a tether; and Y is selected from

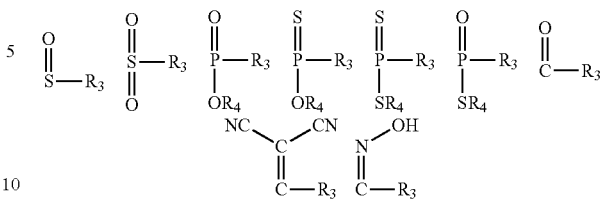

where $R_3$ is alkyl, substituted alkyl, aryl, substituted aryl, $SR_5$, $OR_5$, $NHR_5$, or $NR_5R_6$, $R_4$ is alkyl, substituted alkyl, aryl or substituted aryl, and $R_5$ and $R_6$ are alkyl, substituted alkyl, aryl or substituted aryl; and wherein if Y is

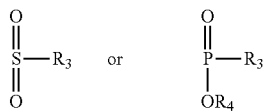

and the bridge atoms are both C then $R_3$ is not $OR_5$ and wherein if Y has two R groups they may be distinct or combined in a cyclic or heterocyclic structure.

2. The method of claim 1, wherein $R_1$ is a substituted or unsubstituted trans, trans-farnesyl or an all trans-geranylgeranyl group.

3. The method of claim 1, where X is S, Se, SO, $SO_2$, O, NH, NR, or $CH_2$.

4. The method of claim 1 wherein the salt forming basic or acidic group is selected from the group consisting of amino, carboxylic acid, sulfonic, and phosphoric.

5. The method of claim 1 wherein Y imparts selectivity between PMPMEase isoforms.

* * * * *

UNITED STATES PATENT AND TRADEMARK OFFICE
CERTIFICATE OF CORRECTION

PATENT NO. : 7,897,604 B2  Page 1 of 1
APPLICATION NO. : 12/098712
DATED : March 1, 2011
INVENTOR(S) : Nazarius Saah Lamango It is certified that error appears in the above-identified patent and that said Letters Patent is hereby corrected as shown below:

Specification

Column 1 should read

This invention was made with government support under grant GM 08111-35 awarded by NIH/NIGMS/MBRS/SCORE and grant G12 RR0 3020 awarded by Pharmaceutical Research Center NIH/NCRR. The government has certain rights in the invention.

Signed and Sealed this
Third Day of November, 2015

Michelle K. Lee
*Director of the United States Patent and Trademark Office*